United States Patent [19]
Yabe et al.

[11] Patent Number: 5,545,121
[45] Date of Patent: Aug. 13, 1996

[54] COVER-TYPE ENDOSCOPE APPARATUS

[75] Inventors: Hisao Yabe, Hachioji; Yoshihiro Iida, Tama; Akira Suzuki; Hideo Ito, both of Hachioji; Yoshio Tashiro, Hino; Minoru Yamazaki, Hachioji; Osamu Tamada, Hachioji; Shigeru Nakajima, Hachioji, all of Japan

[73] Assignee: Olympus Optical Co., Ltd., Tokyo, Japan

[21] Appl. No.: 26,567

[22] Filed: Mar. 4, 1993

[30] Foreign Application Priority Data

Feb. 2, 1993 [JP] Japan .................................. 5-2366
Feb. 2, 1993 [JP] Japan .................................. 5-2367
Feb. 2, 1993 [JP] Japan .................................. 5-2370

[51] Int. Cl.⁶ .................................................... A61B 1/04
[52] U.S. Cl. ........................ 600/121; 600/124; 206/438; 206/363
[58] Field of Search ................ 128/4, 6; 434/258, 434/259, 262, 276, 283, 367, 433; 206/438, 363, 459.1; 604/164, 165, 189, 280; 600/121, 122, 124, 125

[56] References Cited

U.S. PATENT DOCUMENTS

| | | | |
|---|---|---|---|
| 4,621,735 | 11/1986 | Loon et al. | 206/438 |
| 4,646,722 | 3/1987 | Silverstein et al. | 128/4 |
| 4,825,850 | 5/1989 | Opie et al. | 128/4 |
| 4,886,049 | 12/1989 | Darras | 128/4 |
| 4,947,827 | 8/1990 | Opie et al. | 128/4 |
| 5,025,778 | 6/1991 | Silverstein et al. | 128/4 |
| 5,044,494 | 9/1991 | Tamura | 206/438 X |
| 5,133,336 | 7/1992 | Savitt et al. | 128/4 |
| 5,154,164 | 10/1992 | Chikama | 128/4 |
| 5,201,908 | 4/1993 | Jones | 128/4 |
| 5,237,984 | 8/1993 | Williams, III et al. | 128/4 |

FOREIGN PATENT DOCUMENTS

| | | | |
|---|---|---|---|
| 0302216 | 12/1989 | Japan | 128/4 |
| 325138 | 11/1992 | Japan | 128/4 |

*Primary Examiner*—Richard J. Apley
*Assistant Examiner*—Beverly M. Flanagan
*Attorney, Agent, or Firm*—Armstrong, Westerman, Hattori, McLeland & Naughton

[57] ABSTRACT

A cover-type endoscope apparatus comprising an endoscope cover and a covering endoscope used by inserting said covering endoscope into the endoscope cover. A display means for indicating a fitness of the endoscope cover and the covering endoscope is provided on either the endoscope cover or the covering endoscope.

7 Claims, 16 Drawing Sheets

```
D F 4  / 5 5 0
D F 5  / 5 5 0
D F 9  / 1 0 3 0
D F 11 / 1 3 0 0
D S 9  / 1 1 0 0
R F 5  / 5 5 0
D F 9  / 1 6 0 0
D F 11 / 1 6 0 0
R S 9  / 1 1 0 0
```

- EFFECTIVE LENGTH (mm)
- OUTER DIAMETER OF COVER (mm)
- OBSERVING DIRECTION: F···FORWARD VIEWING, S···SIDE VIEWING
- CROSS-SECTIONAL SHAPE: D···SEMICIRCULAR, R···CIRCULAR

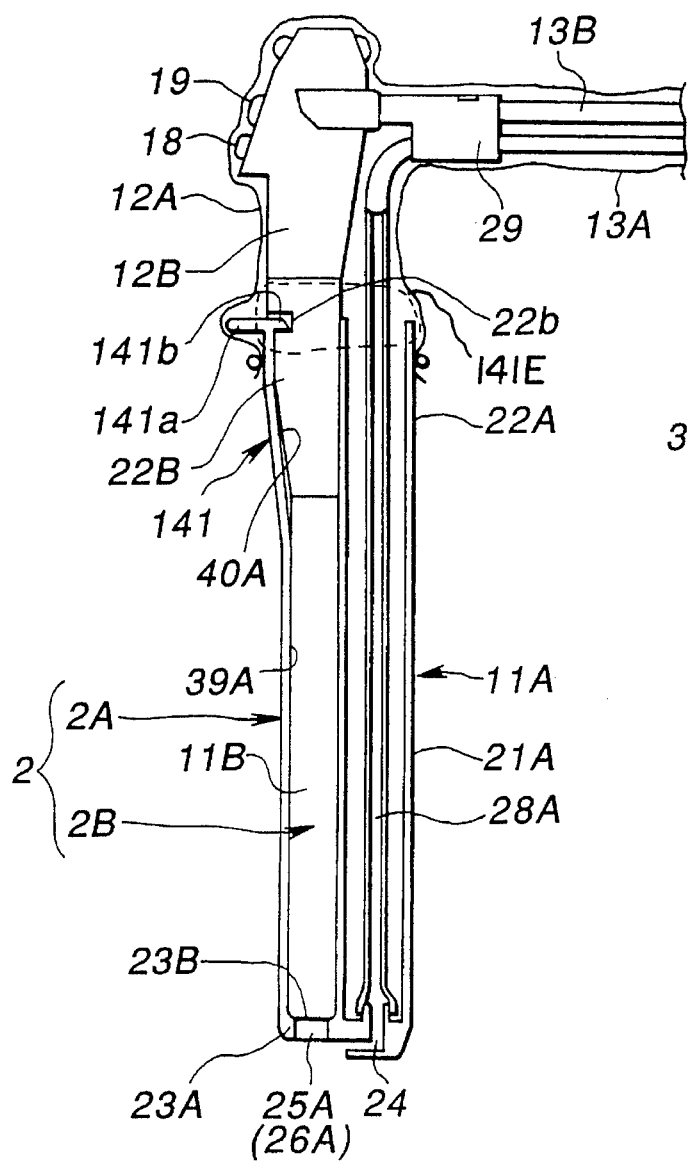
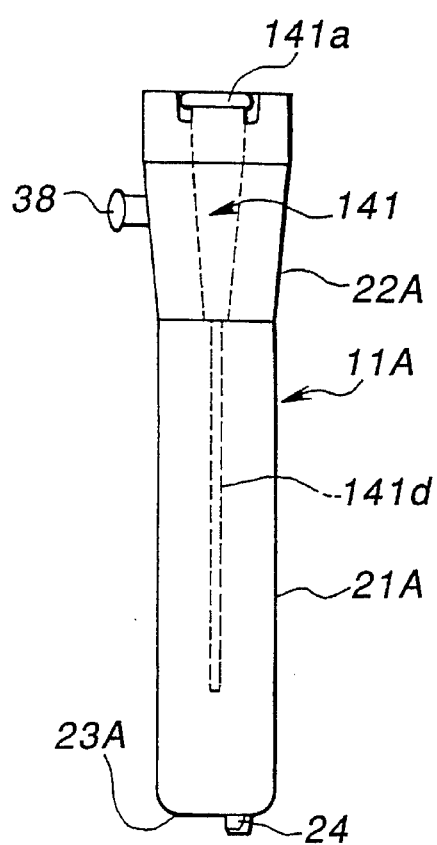
FIG. 10
FIG. 11

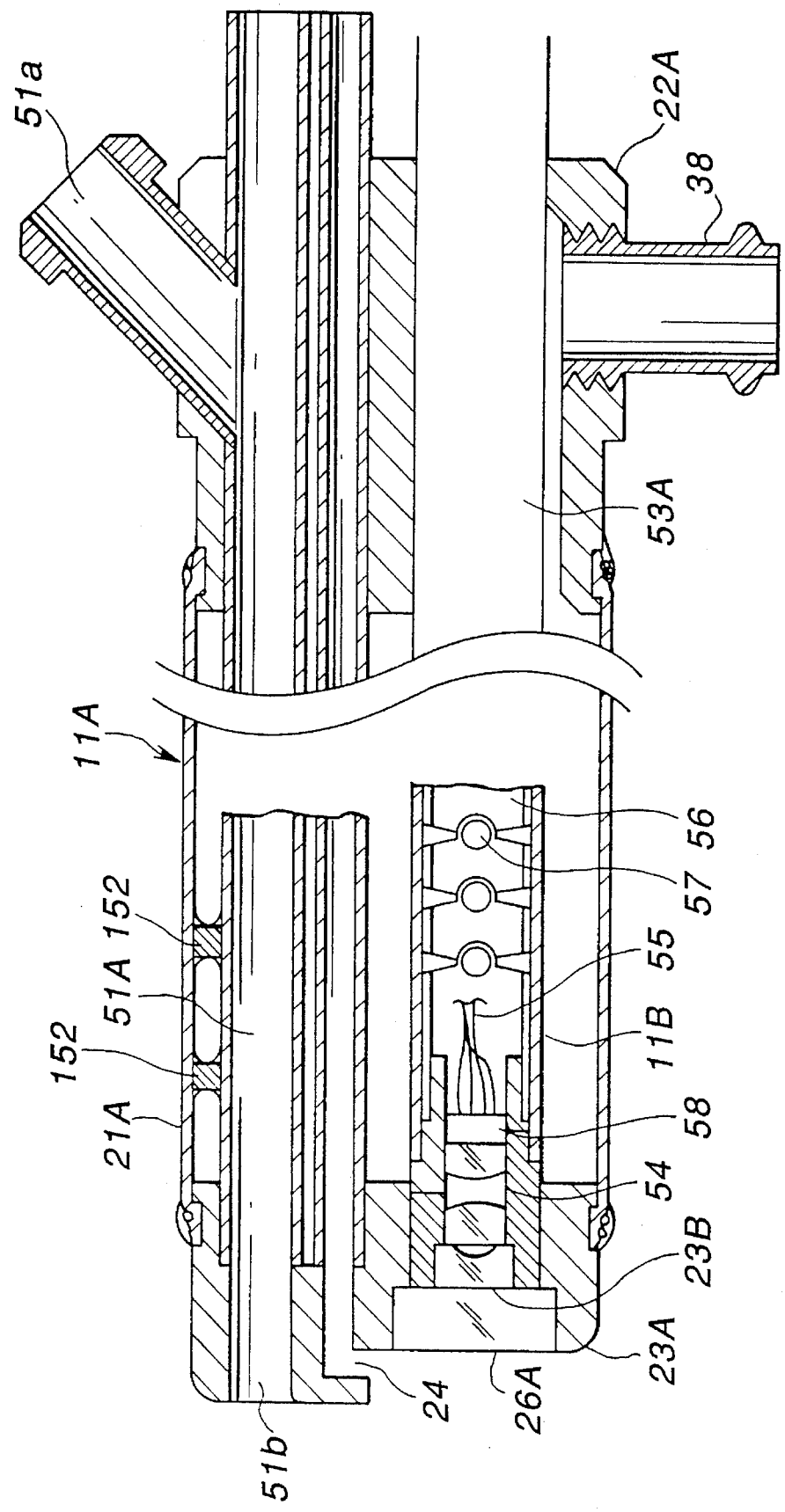

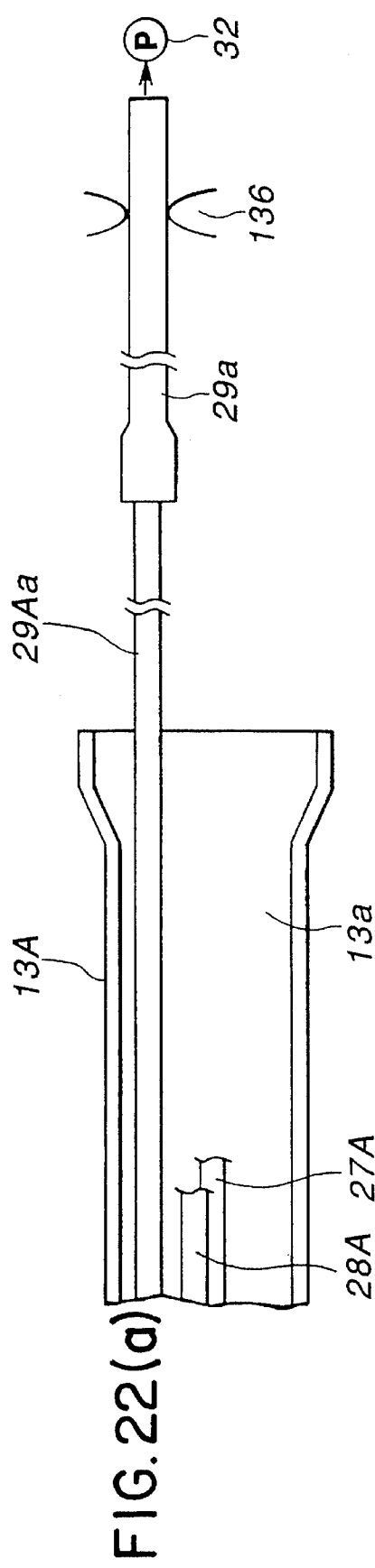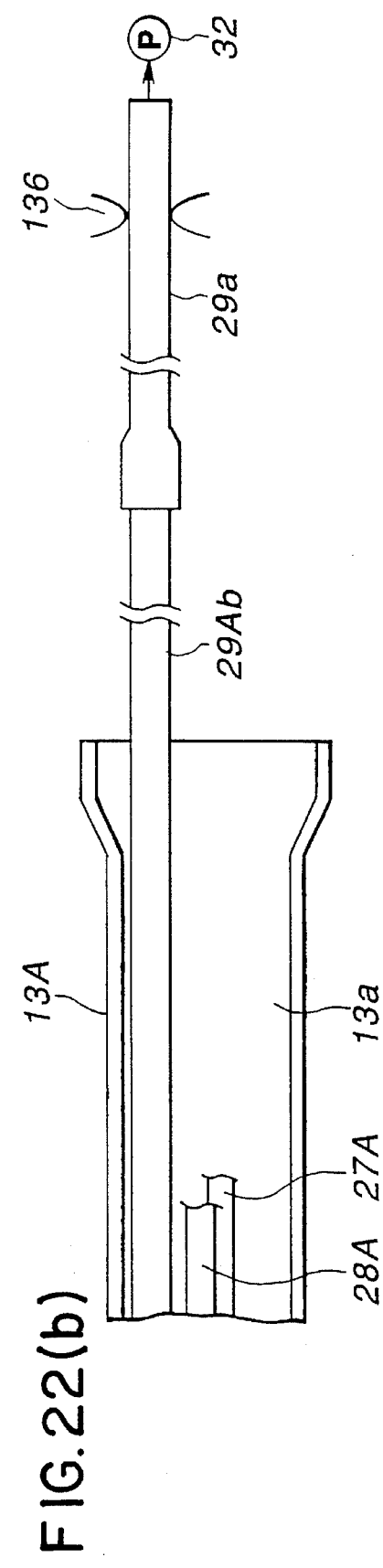

COVER-TYPE ENDOSCOPE APPARATUS

BACKGROUND OF THE INVENTION

1. Field of the Invention

The present invention relates to a cover-type endoscope apparatus for inserting a covering endoscope into an endoscope cover.

2. Description of the Related Art

Recently, endoscopes have been widely used in the medical field. Such an endoscope used in the medical field sometimes cannot provide a sufficiently observable image, when inserted into a living body, because an observing window provided at a distal end of the inserting portion may be smudged by the mucus of a diseased part. Therefore, the endoscope is constructed to have air-supplying/water-supplying functions for supplying water to the observing window for washing and blowing out the residual water by supplying air thereto, by an operation at the proximal side of the endoscope. Further, this air-supplying function can also be used for supplying air into a body cavity to enable easy observation of the portion of interest. The air and the water are supplied through an air supplying duct line or a water supplying duct line.

Other types of endoscopes include one having an aspiratory duct line for aspirating and discharging unnecessary mucus, and one having a forceps channel (treatment channel) to enable sampling a tissue by means of a biopsy forceps or therapeutic treatment using a treatment equipment.

Such endoscopes for the medical field, once used for a patient, would be subject to a washing or sterilizing process for securely preventing any infection.

However, a significant amount of time is required to complete the washing or sterilizing operation, thereby degrading the handling property and use efficiency of the endoscope.

In particular, since the aforementioned duct lines communicate to the outside of the living body from a distal end opening portion opened to a body cavity of the patient through the duct lines of the inserting portion, the distal end opening portion and the inside of the duct lines should also be washed and sterilized. This operation requires a significant amount of time and is troublesome.

Therefore, in recent years, there has been used one kind of an endoscope apparats, a so-called "cover-type" endoscope, in which the endoscope itself is covered with an endoscope cover which is thrown away after every use, thereby simplifying the washing and sterilizing processes.

According to this cover-type endoscope, a duct line opened in a body cavity of a patient is provided at the endoscope cover side, while an observing means not opened to the body cavity of the patient and an illuminating means are provided at the endoscope side to be covered with the endoscope cover. As a result, the video endoscope is not left unclean even when using a quite expensive video endoscope incorporating a solid imaging device (SID) capable of easily displaying the image on a monitor by excellent properties of the illuminating means, high image quality and demonstrating characteristics. Further, it is possible to simplify the washing and sterilizing processes by dumping the endoscope cover.

This so-called cover-type endoscope is disclosed in U.S. Pat. No. 4,646,722 or U.S. Pat. No. 3,162,190, for example.

There are a great number of kinds of endoscopes since the outer diameter, length, field of view of the inserting portion of the endoscope are determined in accordance with the function and the diseased part of interest. Therefore, it is almost impossible to include all desirable features of an endoscope to be used. In particular, in a cover-type endoscope apparatus used as a combination of a covering endoscope and an endoscope cover, it is necessary to select a proper endoscope cover which would fit the respective covering endoscope each time. If the selected combination is improper, the essential functions of the endoscope cannot be sufficiently and totally brought out.

Further, such a cover-type endoscope is used for inspection, by fitting the endoscope cover to a covering endoscope for preventing inter-patients or inter-hospital infections. Therefore, a soiled, used endoscope cover is thrown away upon completion of an inspection for mounting a new one for the next case. However, it is not easy to distinguish between a used cover and an unused one, which requires a significant amount of time and labor.

On the other hand, a proximal (hand-side) end portion of water-supplying/air-supplying duct lines, an aspiratory duct line and the like provided at the endoscope cover side is coupled to an external connecting device (fluid controlling device) through a connecting portion. The external connecting device is provided with a pump and an electromagnetic valve for air-supplying, water-supplying and aspirating in response to an operation of a switch mounted on an operational portion side of the endoscope. However, the air is a compressible fluid while the liquid is an incompressible fluid, and it is necessary to set the inner diameters of the duct lines to proper sizes for obtaining a correct flow amount in view of the flow resistance of the respective duct line. Therefore, it is typical, for example, to have the inner diameter of the air-supplying duct line different from that of the water-supplying duct line.

The endoscope cover is selected in accordance with the covering endoscope to be used, so that the connection of the duct line with the external connecting device would be made by the user. At this time, if the user erroneously connects, for example, the air-supplying duct line instead of the water-supplying duct line to the device, the fluid being water or air would be supplied through a duct line of unsuitable inner diameter. Namely, if air is supplied through a water-supplying duct line, the supplied amount of air would become excessive. Meanwhile, if water is supplied through the air-supplying duct line, the desired amount of water cannot be obtained, thereby impeding the inspection. The same problem would arise when the aspiratory duct line is erroneously connected to the device.

SUMMARY OF THE INVENTION

It is therefore an object of the present invention to provide an improved cover-type endoscope which is easy-handling and is capable of preventing mis-connection of the duct lines by enabling the user to ensure at a glance the fitness in combination of an endoscope cover and a covering endoscope.

It is another object of this invention to provide an improved cover-type endoscope which is easy-handling and capable of preventing mis-use by enabling the user to easily distinguish the endoscope covers being used and unused states at a glance.

It is another further object of this invention to provide an improved cover-type endoscope which is easy to handle and capable of preventing mis-connection of the duct lines by enabling the user to discriminate the duct lines at a glance when the duct lines derived from the endoscope are connected to an external connecting device.

In summary, a cover-type endoscope apparatus according to the present invention comprises an endoscope cover and a covering endoscope used by inserting the covering endoscope into the endoscope cover, wherein a display means for indicating the fitting in combination of the endoscope cover and the covering endoscope is provided.

The above and other advantages, features and additional objects of this invention will be apparent to those of ordinary skill in the art upon making reference to the following detailed description and the accompanying drawings in which a structural embodiment incorporating the principles of this invention is shown by way of illustrative example.

BRIEF DESCRIPTION OF THE DRAWINGS

FIG. 6 is a cross-sectional view of an inserting portion-covering portion according to the third embodiment of this invention;

FIG. 7 is a cross-sectional view of FIG. 6 cut out along a line VII—VII;

FIG. 8 is a cross-sectional view of the inserting portion-covering portion;

FIG. 9 is a cross-sectional view of FIG. 8 cut out along a line IX—IX;

FIGS. 10 through 12 show a fourth embodiment of the present invention;

FIG. 10 is a cross-sectional view of an endoscope of channeled endoscope covering type;

FIG. 11 is a side view of the inserting portion-covering portion;

FIG. 12 is a cross-sectional view of the inserting-portion covering portion;

FIGS. 14 and 15 show a sixth embodiment of the present invention;

FIG. 14 is a perspective view showing a welding-fusing apparatus;

FIG. 16 is a schematic view of a cover-type endoscope apparatus;

FIG. 17 is a cross-sectional view of a universal cord at the proximal end portion;

FIGS. 19–21 show a ninth embodiment of the present invention;

FIG. 19 is a cross-sectional view of an inserting portion-covering skin;

FIG. 20 is a cross-sectional view of an inserting portion-covering portion in the longitudinal direction;

FIGS. 22(a) and 22(b) show cross-sectional views of a universal cord cover, at the proximal side, provided with aspiratory duct lines with different diameters according to a tenth embodiment of this invention.

DETAILED DESCRIPTION OF THE PREFERRED EMBODIMENTS

FIGS. 1 through 4 of the accompanying drawings show a first embodiment of the present invention.

Figure 1:
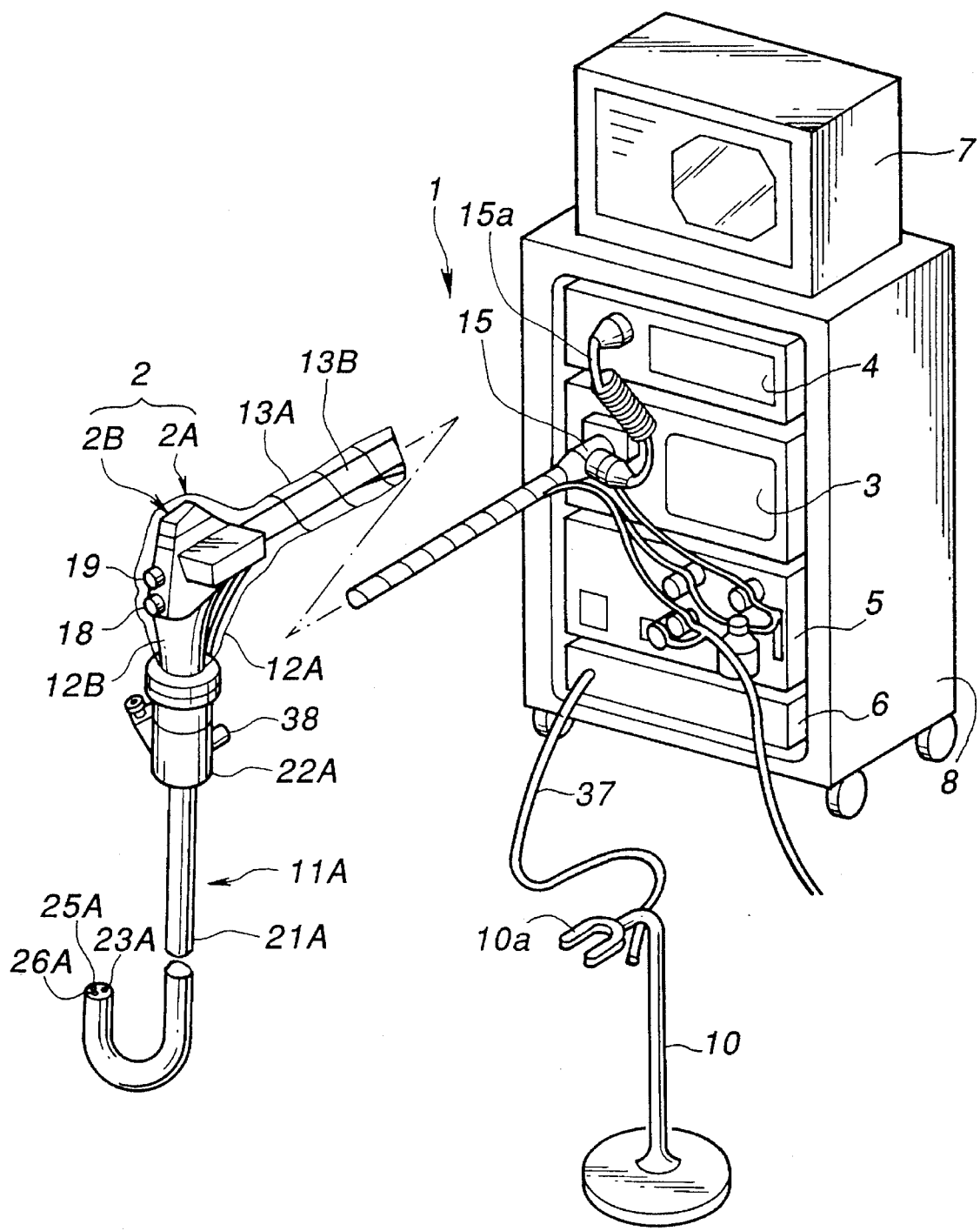
FIG. 1 is a perspective view of a cover-type endoscope apparatus.

As shown in FIG. 1, a cover-type endoscope apparatus 1 according to the present invention includes: an endoscope of channeled endoscope cover type (hereinafter referred to as "cover-type endoscope") 2 composed of a channeled endoscope cover (hereinafter referred to as "cover") 2A and a channeled endoscope-covering type endoscope 2B fitted to the cover 2A (hereinafter referred to as "covering endoscope"); a light source device 3 for supplying illuminating light to the covering endoscope 2B; a video processor 4 for processing signals for an imaging means incorporated into the covering endoscope 2B; a flow controlling device 5 for supplying air and water through a tube of the cover 2A; an endoscope cover expander (hereinafter referred to as "expander") 6 used for fitting the covering endoscope to the cover 2A; and a monitor 7 for indicating image signals having been processed by the video processor 4. The light source device 3, the video processor 4, the fluid controlling device 5, and the expander 6 are accepted in the cart 8, on which the monitor 7 is disposed.

For performing an endoscope inspection, the covering endoscope is covered with the clean unused cover 2A, which is thrown away after completion of the inspection. On the other hand, the covering endoscope 2B is covered with a new clean cover 2A and repeatedly used.

When the covering endoscope 2B is fitted to the inserting portion cover 11A composing the cover 2A, a cover holding member 10 shown in FIG. 1 is used. For example, an endoscope inserting portion 11B of the covering endoscope 2B is fitted by engaging the base end side of the inserting portion-covering portion 11A with a cover holding member 10a, for example.

The covering endoscope 2B is composed of an elongated flexible endoscope-inserting portion (hereinafter referred to as "inserting portion") 11B, an endoscope operational portion (hereinafter referred to as "operational portion") 12B formed at the base end side of the inserting portion 11B, and a universal cord 13B extending from a side portion of the operational portion 12B. The inserting portion 11B includes an illuminating optical system and an objective optical system for imaging an object on the imaging means at its distal end. Further, by connecting the connector 15 provided at the end of the universal cord 13B to the light source device 3, the illuminating light from the lamp incorporated into the light source device 3 is supplied to the illuminating light system through a light guide (not shown) inserted into the universal cord 13B and a light guide inserted to pass through the inserting portion 11B.

The illuminating light supplied to the illuminating optical system is then emitted to a forward object through a transparent plate of a cover illuminating window 25A provided at an end surface of a cover distal end portion 23A of the inserting portion-covering portion 11A opposed to an illuminating window (not shown) of a distal end 23B of the inserting portion 11B.

The object, such as a diseased part, which was illuminated is imaged as an optical image on an imaging surface of the imaging means such as a solid imaging device (SID) provided on a focused surface through a transparent plate of a cover observing window 26A mounted contiguously with a cover illuminating window 25A and an objective optical system mounted on the inserting portion 11B of the covering endoscope 2B disposed at the inner side of and opposed to the cover observing window 26A.

The optical image formed on the imaging surface is photoelectrically converted and input to the video processor 4 through the inserting portion 11B and a signal cable 15a passed through the universal cord 13B, and after signal-processing, a standard image signal is created to be input to the monitor 7 for providing an object image on the display screen.

Further, the operational portion 12B of the covering endoscope 2B comprises: air-supplying and/or water-supplying (or only water-supplying) switch 18; an aspiratory switch 19; an image switching switch 20; and a curved operational knob (not shown) mounted thereon. By operating the respective switch, the air and/or water supplying (or only the water-supplying), aspiration, or image switching such as freezing or releasing of the image switching, and the curved angle of a distal curved portion provided at the inserting portion 11Ba are set.

On the other hand, the cover 2A is composed of the inserting portion-covering portion 11A, the operational portion cover 12A, and the universal cord cover 13A for covering, respectively, the inserting portion 11B of the covering endoscope 2B, the operational portion 12B, and the universal cord 13B.

The inserting portion cover 11A comprises an inserting cover skin 21A for covering the inserting portion 11B, an opening portion 22A for fixing the operational portion of the endoscope provided airtightly at the base end of the inserting portion cover skin 21A, and a cover distal end portion 23A provided airtightly at an end portion of the inserting cover skin 21A.

Figure 2:
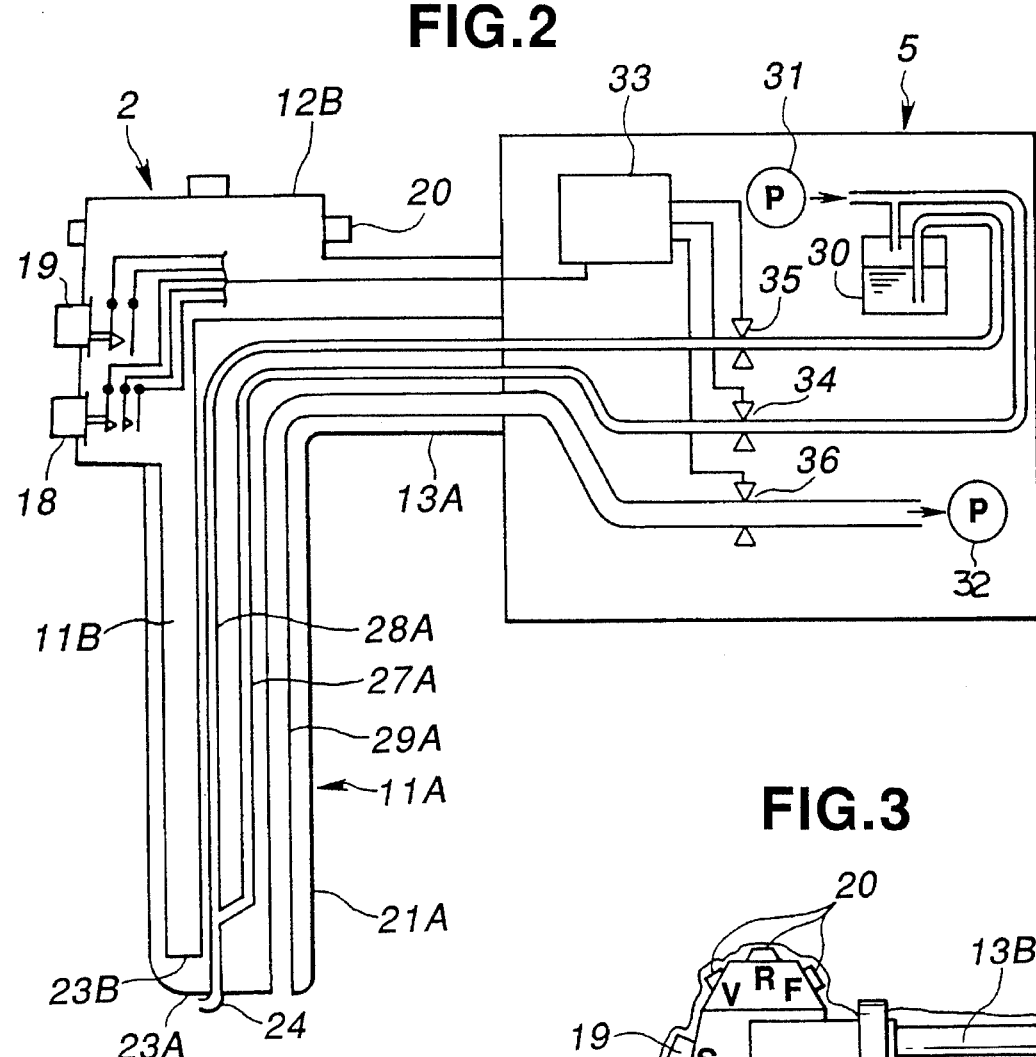
FIG. 2 is a schematic view of a cover-type endoscope apparatus.

As shown in FIG. 2, the inserting portion cover 11A comprises an air-supplying duct line 27A, a water-supplying duct line 28A and an aspiratory duct line 29A. The air-supplying duct line 27A and the water-supplying duct line 28A are mated at the distal end side to communicate with a nozzle 24 provided at the end surface of the cover distal end portion 23A, and the distal end opening of the nozzle 24 is opposed to the external surface of the cover observing window 26A.

Further, the base end sides of the air-supplying duct line 27A, water-supplying duct line 28A, and the aspiratory duct line 29A are extended toward the upper side of the opening portion 22A for fixing the operational portion of the endoscope, and are also extended toward the fluid controlling device 5 side in a state of being covered with the universal cord cover 13A together with the universal cord 13B. The water-supplying duct line 28A is opened to the water-supplying tank 30. The air-supplying duct line 27A communicates with the air-supplying pump 31, having an intermediate portion branched off and opened to the upper part of the water-supplying tank 30. Further, the aspiratory duct line 29A communicates with the aspiratory pump 32.

The air-supplying/water-supplying switch 18 is a double switch in which during the first depressing operation its air-supplying electromagnetic valve 35 opens to supply air though the air-supplying pump 31, and during the second depressing operation its water-supplying electromagnetic valve 35 opens to supply water stored in the air-supplying tank. During the second depressing operation, the air-supplying electromagnetic value 34 can be either opened or closed.

Meanwhile, when the aspiratory switch 19 is depressed, an aspiratory electromagnetic valve 36 opens and the aspiratory operation by the aspiratory pump 32 starts.

Therefore, body fluids adhered to the cover observation window 36A can be adhered by supplying air or water through the air-supplying duct line 27A or the water-supplying duct line 28A by the operation of the air-supplying/water-supplying switch 18.

In addition, a dilatable tube mouth 38 for connecting a dilatable tube 37 to the dilator 6 is provided at the side surface of the mouth 22A for fixing the endoscope operational portion.

Further, an opening 40 of the endoscope inserting channel 39 for receiving the inserting portion 11B of the covering endoscope 2B is provided on the upper surface of the mouth 22A for fixing the endoscope operational portion. The endoscope inserting channel 39 allows insertion of the covering endoscope 2B except for the cover distal portion 23A, cover skin 21A of the inserting portion, and a part of the inner space surrounded by the mouth 22A for fixing the endoscope operational portion except for the air-supplying duct line 27A, water-supplying duct line 28A and the aspiratory duct line 29A.

The dilator 6 normally continually supplies air. Therefore, when the dilator 6 is not in use, the end of the dilatable tube 37 is disconnected from the dilatable tube mouth 38 and exposed to the air. Inserting of the covering endoscope 2B into the inserting portion-covering portion 11 is carried out in an air-tight manner by pressing out the end of the dilatablue tube 37 into the dilatable tube mouth 38. The air supplied from the dilator 6 is then fed to the endoscope inserting channel 39 through the dilatable tube mouth 38 to dilate the endoscope inserting channel 39 to help the inserting operation of the inserting portion 11B.

Figure 3:
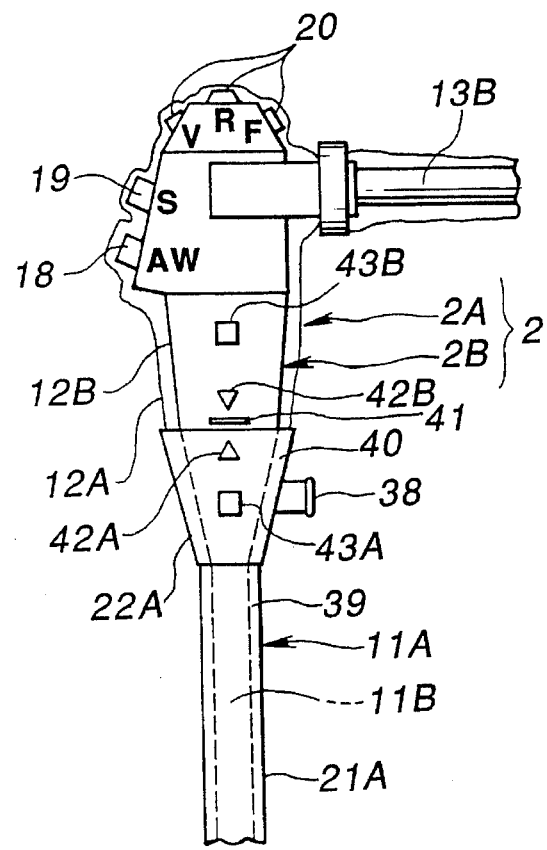
FIG. 3 is a side view of an endoscope of a channeled endoscope-covering type.

As shown in FIG. 3, there are indications, on the body surfaces of the operational portion 12B and the covering endoscope 2B, of the operational functions of the switches 18, 19, 20 and of the knob, AW, S, F, R, V etc. corresponding to the air-supplying/water-supplying switch 18, the aspiratory switch 19, the image changing switches 20 and a curving operational knob (not shown) etc. These indications are expressed by white letters on the surface of black-colored operational portion 12B using silk printing. Also, these indications can be made by using molded products of the color letters secured to the body surfaces of the operational portion 12B and the covering endoscope 2B, in which case it would also be possible to form convex and concave surfaces to enable the indication to be identified by an operator's finger touch. The indications can further include not only the operational functions, but also operational methods, operational directions, and operational means. Furthermore, the indications can include other identifiable items than letters, e.g. words, colors and patterns.

The operational portion cover 12A covering the operational portion 12B can preferably be formed of a transparent or a semitransparent soft resin such as fluorocarbon rubber, or thin-film Teflon etc.

As shown in FIG. 3, positional indices 41, 42A, and 42B are provided on the side surface of the inserting portion-covering portion 11A and on the operational portion 12B of the covering endoscope 2B. The triangle positional indices 42A and 42B are opposed to each other with a bar-type positional index 41 therebetween, which enable the operator to easily confirm the correct disposition of the inserting portion-covering portion 11A with respect to the covering endoscope 2B. As a result, it becomes possible to prevent an unexpected falling of the inserting portion-covering portion 11A during the inspection due to its uncertainly mounted condition which would cause the covering endoscope 2B to be contaminated.

Also, at the operational portion 12B of the covering endoscope 2B and at the side surface of the inserting portion-covering portion 11A, display means 43A and 43B representing the features of the cover-type endoscope 2 by codes etc. are provided for enabling the recognition of the features at a glance. Items representing the features of the cover-type endoscope 2 include: observing direction such as direct view or side view; length of the inserting portion; outer diameter of the inserting portion; inner diameter of the duct lines, and direction capable of being curved of the distal end portion of the inserting portion, etc.

As means for describing such features, predetermined letters, codes, colors or combinations thereof can be used. Further, there is no limitation for the displaying position, and any viewable position on the cover-type endoscope 2 composed of the covering endoscope 2B and the cover 2A can be used.

Figure 4:
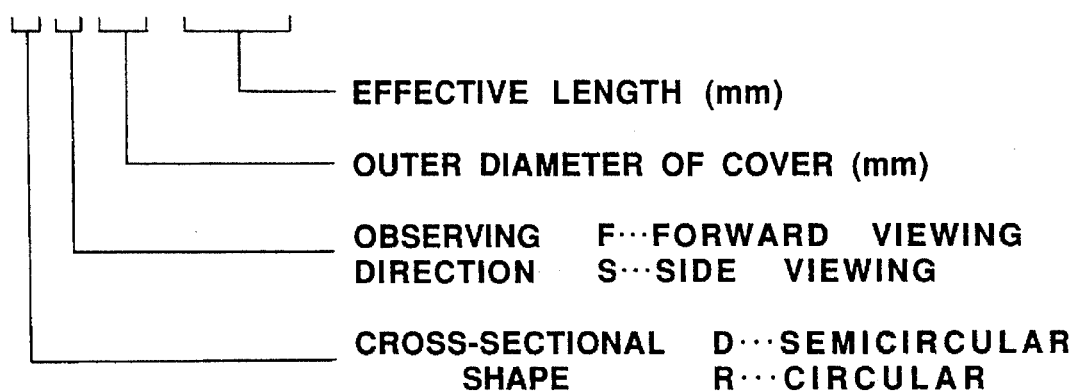
FIG. 4 is a table showing contents indicated by a display means.

FIG. 4 shows examples of the indications of the display means 43A and 43B for the respective type thereof. For example, from an indication "DF11/1600" displayed on the display means 43A and 43B, the operator can identify a covering endoscope 2B and a cover 2A used for a cover-type endoscope 2 having an inserting portion-covering portion 11A with 11 mm of outer diameter and 1600 mm of effective length.

In addition to the above-mentioned items, an outer diameter (diameter) of the inserting portion 11B of the covering endoscope 2B and an inner diameter of the forceps channel can also be displayed.

The operation of this embodiment will now be described.

First, after determination of the outer diameter and the effective length etc. of the endoscope used in accordance with the purpose and the diseased portion, a proper covering endoscope 2B and a cover 2A for covering the covering endoscope 2B fitted thereto are selected in accordance with the items indicated on the display means 43A and 43B provided on the body surfaces thereof.

As a result, any mis-combination of the covering endoscope 2B and the cover 2A to be fitted to the covering endoscope 2B would not arise so as to simplify the identifying operation.

When the covering endoscope 2B is inserted into the inserting portion-covering portion 11A of the selected cover, a flange portion at the upper end of the mouth portion 22A for fixing the endoscope operational portion is supported by a semi-circular cover holding member 10a provided on a holder 10.

Then an end of the dilatable tube 37 is coupled to the dilatable tube mouth 38 and the covering endoscope 2B is inserted into the opening portion 40 to dilate the inserting portion cover skin 21A to achieve a smooth mounting of the inserting portion 11B. At this time, the positioning operation is performed by aligning the positional index 42B provided on the side surface of the operational portion 12B of the covering endoscope 2B with the positional index 42A provided on the side surface of the inserting portion cover skin 21A. Thus, any mis-mounting can be avoided.

After completion of the inserting process, the end of the dilatable tube 37 is removed from the dilatable tube mouth 38 so as to contract the inserting portion cover skin 21A by its elasticity (the outer diameter of the inserting portion cover skin 21A reduces), thereby closely adhering the skin or outer surface of the inserting portion to the inner surface of the skin 21A.

Further, since the operation portion cover 12A for covering the operational portion 12B of the covering endoscope 2B is transparent or semitransparent, the indications for the operational functions of the operational switches 18 and 19 etc. can be easily recognized from outside, which would contribute to prevent mis-handling during the operation.

Figure 5:
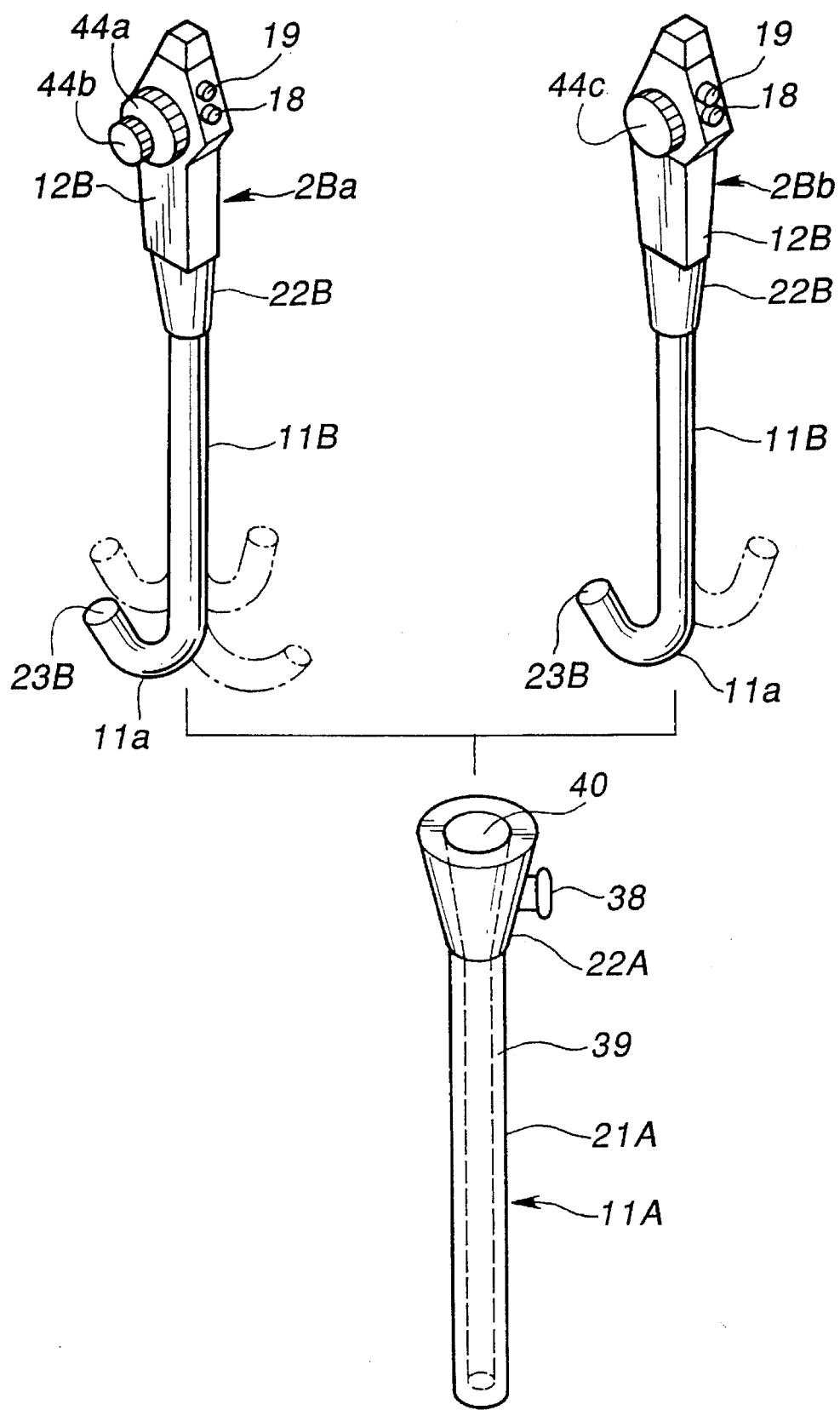
FIG. 5 is a perspective view showing two covering endoscopes having different functions and an inserting portion-covering portion used in common with both covering endoscopes according to the second embodiment of this invention.

FIG. 5 shows a second embodiment of the present invention.

There are two types of the covering endoscope 2B, one type having a distal curved portion 11a capable of being curved in four directions with respect to the axis of the inserting portion 11B, another type having the same portion 11a capable of being curved in only two directions. In this case, the former type is referred to as a cover-type four-directional curved endoscope 11Ba, while the latter type as a cover-type two-directional curved endoscope 11Bb. By operating curved operating knobs 44a and 44b for the vertical and the horizontal directions respectively provided on the operational portio 12B of the cover-type four-directional curved endoscope 11Ba, the four curving directions will be combined to enable the distal end curved portion 11a to be curved in any direction, thereby providing an excellent handling property. On the other hand, by operating a vertical direction curved operating knob 44c provided on the operational portion 12B of the covering two-directional curved endoscope 2Bb, the distal end curved portion 11a could be curved in two dimensions.

The outer diameter and the effective length of the inserting portion 11B of both the covering endoscopes 2Ba, 2bB and that of the mouth mounting portion 22B for fixing the operational portion of the endoscope provided at the base end side of the inserting portion 11B are the same. Meanwhile, the inner diameter of the inserting cover portion 11A to be fitted to the inserting portion 11B of both the covering endoscopes 2Ba, 2Bb and the outer diameter of the inner surface of the mouth portion 22A for fixing the operational portion of the endoscope are equal to the outer diameter of the inserting portion 11B of both the covering endoscopes 2Ba, 2Bb and the inner shape of the mouth mounting portion 22B for fixing the operational portion of the endoscope provided at the base end side of the inserting portion 11B.

As a result, a single inserting portion-covering portion 11A can be used in common for two covering endoscopes 2Ba, 2Bb of different curving directions.

As a related art, conventionally a number of different inserting portion-covering portions 11A should have been prepared for fitting to different outer diameters and cross-sectional shapes of the inserting portion of the covering endoscopes to be used, and for different contours of the mouth mounting portion 22B for fixing the operational portion of the endoscope provided at the base end side of the inserting portion 11B. Therefore, the more the combinations of the fitting, the more the number of mis-fittings. For example, if a covering endoscope 2B for an inserting portion 11B of large diameter is applied to an inserting portion-covering portion 11A of a small diameter, the endoscope operation would be impeded. According to the present invention, such disadvantages due to the mis-fitting of the inserting portion-covering portion can be prevented.

FIGS. 6 through 9 show a third embodiment of the present invention.

Figure 6:
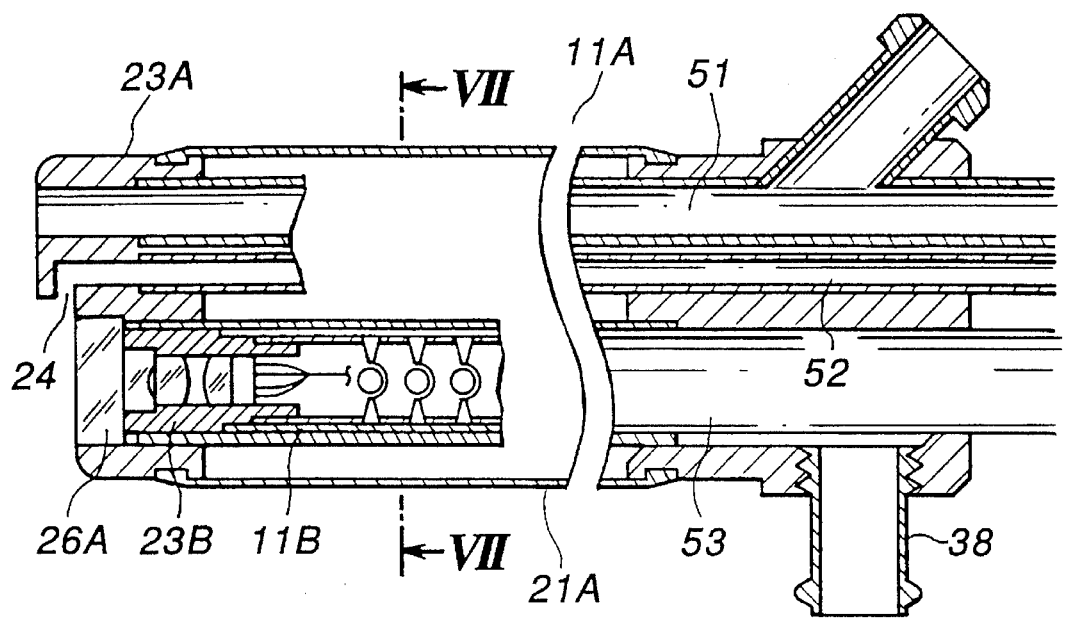
FIGS. 6 through 9 show a third embodiment of this invention.
Figure 7:
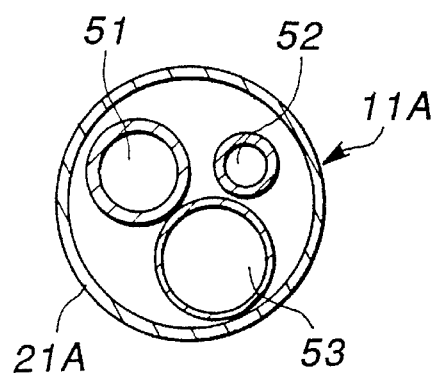
Figure 8:
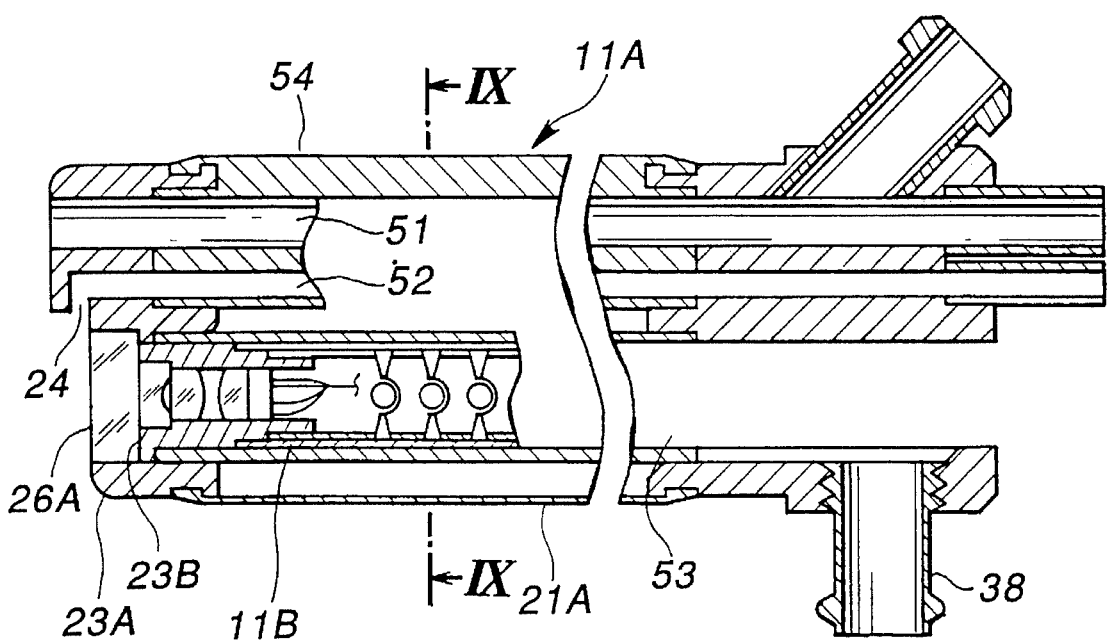
Figure 9:
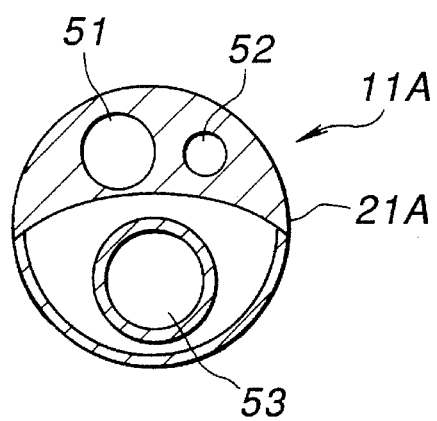

As shown in FIGS. 6 and 7, as a related art of this invention, an endoscope is known in which a channel tube 51, an air-supply/water-supply duct line 52, and an endoscope inserting channel 53 etc. are independently and separately mounted on the inserting portion-covering portion 11A. In this related art, for example, during insertion of a forceps or a covering endoscope 2B into the channel tube 51 and the endoscope inserting channel 53, the channel tube 51 or the endoscope inserting channel 53 meander in the cover portion 11A for the inserting portion. As a result, there have been disadvantages in that the forceps or the covering endoscope 2B cannot be smoothly inserted, that the air/water supply is impeded by rupture of the air-supply/water-supplying duct line 52, and that the duct line would be damaged.

In view of this, according to this invention, the cover skin 21A for the inserting portion of the cover portion 11A for the inserting portion is formed of multi-lumen tubes composed by integrating the channel tube 51 and the air-supplying/water-supplying duct line 52.

As a result, even if the covering endoscope 2B is inserted, any duct line would meander in the cover portion 11A for the inserting portion, thereby making the inserting operation smoother and improving the durability of the duct lines by preventing the components from being damaged.

Figure 12:
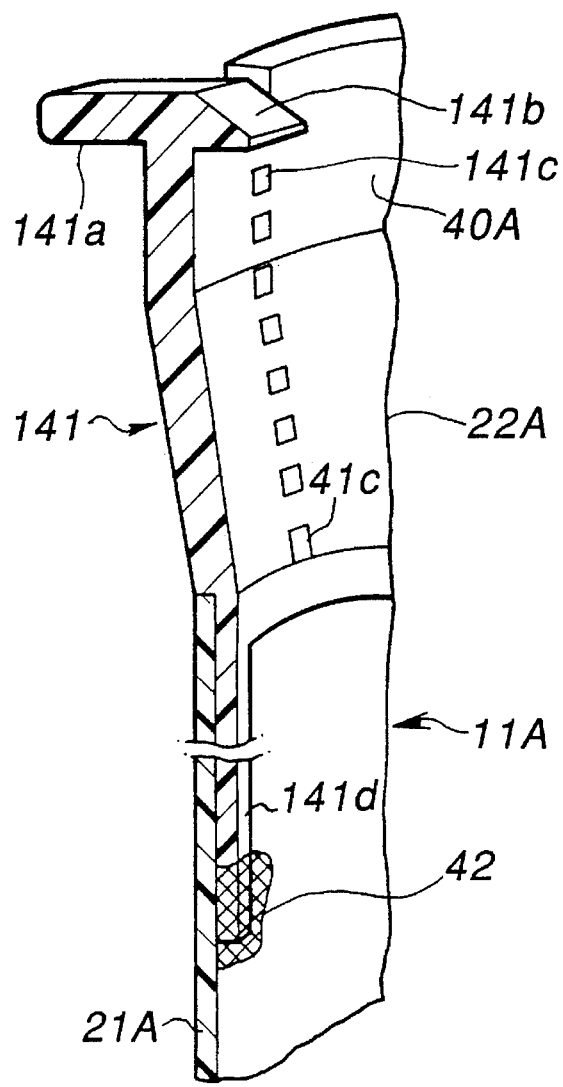

FIGS. 10 through 12 show a fourth embodiment of the present invention.

As shown in FIG. 10, a water-supplying duct line 28A and an endoscope inserting channel 39A etc. are provided in the cover portion 11A for the inserting portion.

The water-supplying duct line 28A communicates with the nozzle 24 provided at the end surface of the cover distal end portion 23A, and the end opening of the nozzle 24 is opposed to the outer surface of the cover observing window 26A.

Further, the base end side of the water-supplying duct line 28A extends upwardly from the mouth portion 22A for fixing the operational portion of the endoscope, and toward the fluid controlling apparatus 5 side in a state being covered with a universal cord cover 13A together with the universal cord 13B.

A dilatable tube mouth 38 for connecting a dilatable tube 37 coupled to the dilator 6 is provided at the side surface of the mouth portion 22A for fixing the operational portion of the endoscope. In addition, the upper surface of the mouth portion 22A for fixing the operational portion of the endoscope has an opening 40A of the endoscope inserting channel 39A. The mouth portion 22A for fixing the operational portion of the endoscope is formed of a relatively hard fluorocarbon resin etc., and adhered to the cover skin 21A of the inserting portion made of fluoro rubber by an adhesive agent such as a fluoro adhesive agent.

Further, a holding portion 141a of a rupturing member 141 as an example of the display means is formed at the opening 40A of the mouth portion 22A for fixing the operational portion of the endoscope integrally therewith. An engaging claw 141b is inwardly projected from the holding portion 141a. Meanwhile, a concave 22b engageable with the engaging claw 141b is formed on the mounting portion 22B for the mouth portion for fixing the operational portion of the endoscope and tapered at the base end portion of the inserting portion 11b of the covering endoscope 2B.

In addition, the rupturing member 141 and the opening portion 40A are bordered by perforations 141c formed at every predetermined depth from the inner surface along the longitudinal direction. Further, a rupturing bar 141d extending downwardly from the lower part of the rupturing member 141 is superimposed on the endoscope inserting channel 39A formed at the cover skin 21A for the inserting portion, and the lower end of the bar 141d is fixed by an adhesive agent 42. Alternatively, the rupturing member 141 and the rupturing bar 141d can be composed separately.

The operation of this embodiment will now be described.

Firstly, for inserting the covering endoscope 2B into the cover portion 11A for the inserting portion of the cover 2, a flange portion formed at the upper end of the mouth 22A for fixing the operational section of the endoscope is held by a semicircular cover holding member 10a mounted on the holder 10.

Then, an end of the dilatable tube 37 is connected to the dilatable tube mouth 38, and a distal end of the inserting portion 11B of the covering endoscope 2B is inserted into the endoscope inserting channel 39A through the opening 40A. As a result, the opening 40A is narrowed by the inserting portion 11B and air is fed to the endoscope channel 39 to dilate the endoscope inserting channel 39A.

Thereafter, the distal end of the inserting portion 11B is inserted until it touches the cover observing window 26A formed at the distal end of the endoscope inserting channel 39A.

At this time, an engaging claw on the rupturing member 141 formed at the opening 40A would be elastically expanded along a tapered surface of the mouth mounting portion 22B for fixing the operational portion of the endoscope provided on the covering endoscope 2B. When the inserting portion 11B comes in contact with the observing window 26A, the engaging claw 141b would engage with the concave portion 22b formed in the mouth mounting portion 22B for fixing the operational portion of the endoscope. Thus, the inserting operation ends.

Thereafter, when the end of the dilatable tube 37 is removed from the dilatable tube mouth 38, the endoscope inserting channel 39A deflates due to its elasticity (the outer diameter of the cover skin 21A of the inserting cover reduces), and the outer skin of the inserting portion 11B would be substantially adhered to the inner surface of the channel 39A.

The operational portion 12B of the covering endoscope 2B is then covered with the operational portion cover 12A, and its opened end is closely attached to the upper end of the mouth portion 22A for fixing the operational portion of the endoscope of the inserting portion-covering portion 11A, and the universal cord 13B is covered with the universal cord cover 13A, such that the covering endoscope 2B could be inspected in a tightly sealed state.

On termination of the normal inspection, the holding portion 141a of the rupturing member 141 provided on the mouth portion 22A for fixing the operational portion of the cover portion 11A of the inserting portion is held and pulled together with the operational cover portion 12A. Then, the rupturing member 141 is cut out along the perforations 141c so as to remove the engaging claw 141b projecting inwardly from the holding portion 141a from the concave portion 22B formed in the mouth mounting portion 22B for fixing the operational portion of the endoscope.

Further pulling of the rupturing member 141 causes the rupturing bar 141d thereof to rupture the endoscope inserting channel 39A of the cover portion 11A for the inserting portion so as to expose the inserting portion 11B of the covering endoscope 2B having been inserted into the endoscope inserting channel 39A. Then, the covering endoscope 2B is taken out.

According to such a composition, since the inserting portion-covering portion 11A is intentionally ruptured, it is possible to distinguish the used state or unused state at a glance, thereby preventing mis-use. Furthermore, the covering endoscope 2B can become easily removed from the inserting portion-covering portion 11A.

If the respective cover is fixed by a tape 141E rather than holding member 141, it is also possible to construct the apparatus such that the covering endoscope 2B is taken out by ablating or exfoliating the tape, or that the tape partly remains on the cover to indicate the used state.

Figure 13A:
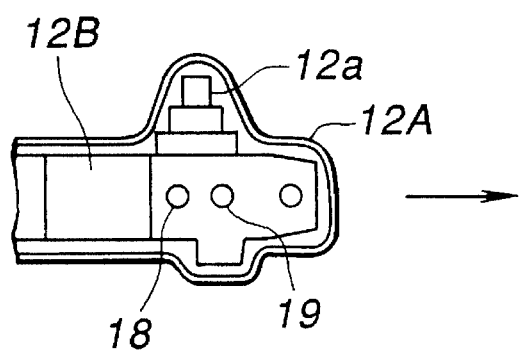
FIGS. 13(a) and 13(b) are side views for each state of an endoscope operational section equipped with an operational portion cover according to the fifth embodiment of the present invention.
Figure 13B:
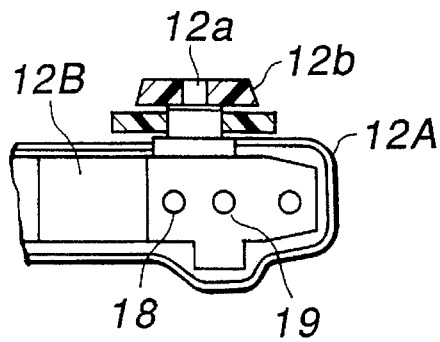

FIG. 13 shows a fifth embodiment of the present invention.

In this embodiment, for fitting a curving operation knob 12b to a curving operation knob shaft 12a provided on the operational portion 12B of the covering endoscope 2B, firstly the operational portion 12B is covered with the operational portion cover 12B. Then the curving operation knob 12b is fitted to a portion of the operational portion cover 12A projecting from the curving operation knob shaft 12a. As a result, the projecting portion would be automatically ruptured by and receives the curving operation knob 12b.

As a related art to the present invention, there is a type of apparatus having a pre-formed hole at a position corresponding to the location of the curving operation knob shaft 12a provided in the operational portion 12B of the operational portion cover 12A. After the operational portion 12B of the covering endoscope 2B is covered with the operational portion cover 12A, the curving operation knob 12a is exposed through the hole and then receives the curving operation knob 12b fitted thereto.

In the above-mentioned related art, the curving operation knob shaft 12a has been easily contaminated because of being already exposed before receiving the curving operation knob 12b. To cope with such a disadvantage, it is preferable, as shown in the embodiment shown in FIG. 13, to construct the apparatus such that the operational portion cover 12A ruptures upon fitting of the curving operation knob 12b to expose the curving operation knob shaft 12a so as to fit the knob 12b without contaminating the knob shaft 12a.

Figure 14:
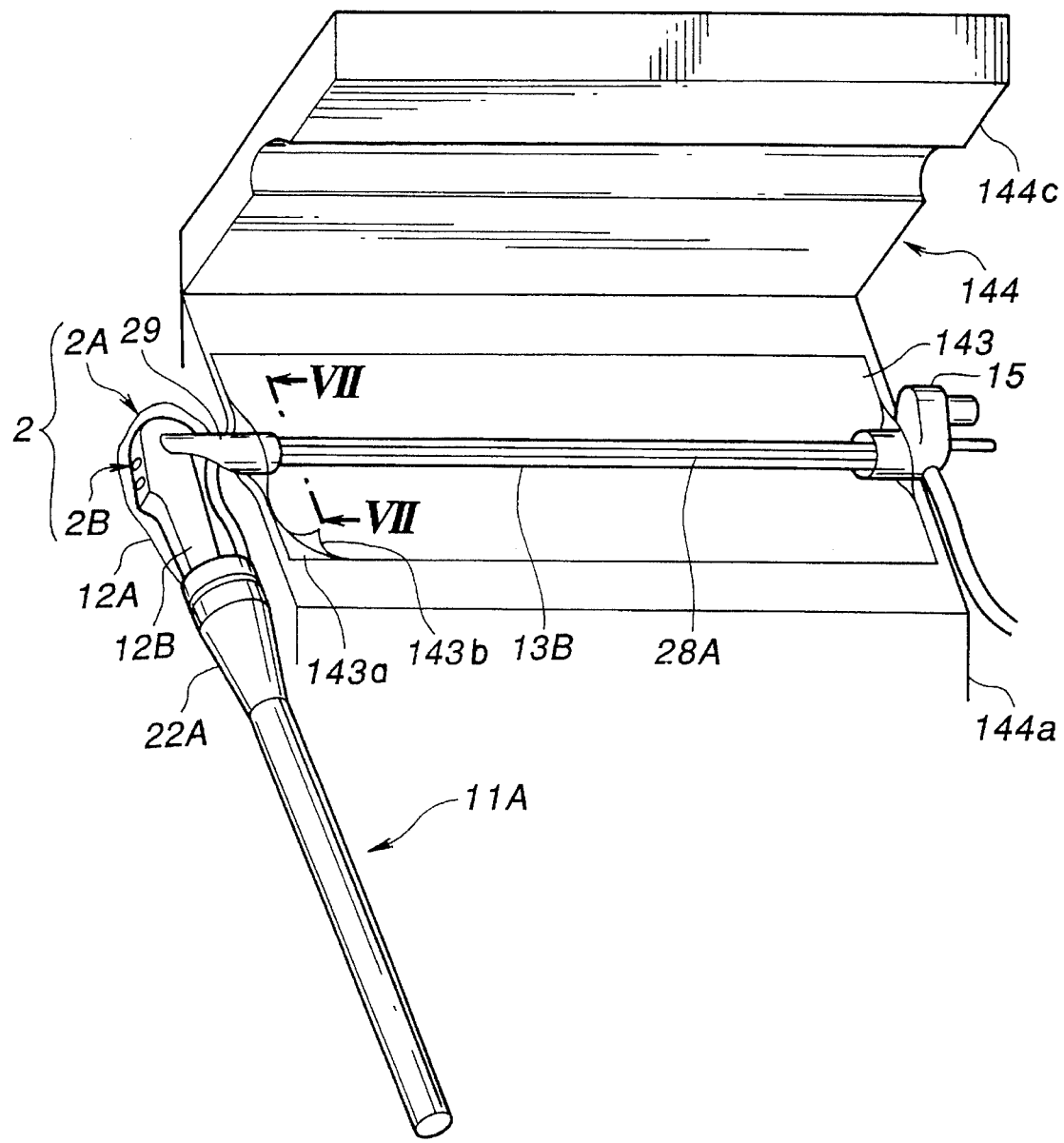
Figure 15A:
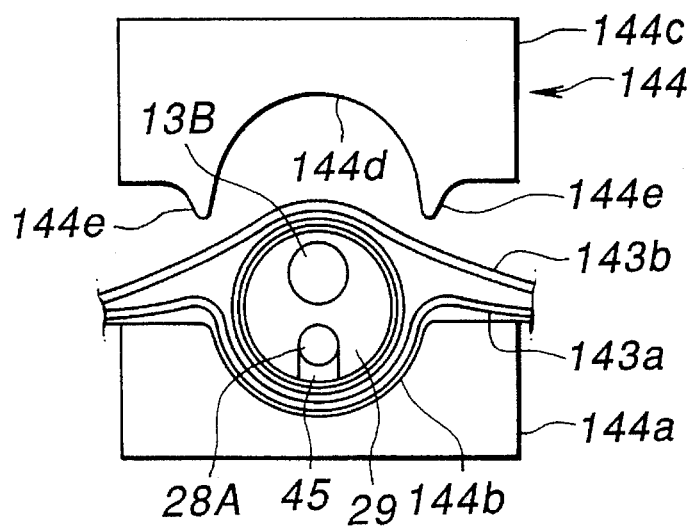
FIGS. 15(a), 15(b) and 15(c) are cross-sectional views for each state in FIG. 14 cut out along a line VII—VII.
Figure 15B:
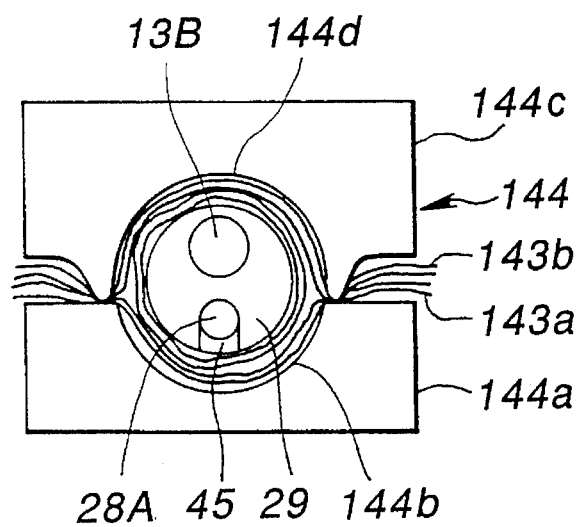

FIGS. 14 and 15 show a sixth embodiment of the present invention.

In this embodiment, by forming the universal cord cover 13A by welding an integral or separate sheet 143 having a first surface 143a and a second surface 143b, it becomes possible to fit the universal cord cover 13A quickly to the universal cord 13B and the water-supplying duct line 28A.

Namely, the sheet 143 is mounted on a welding base 144a of the cover welding device 144, while the holding portion 29, connector 15 and a universal cord 13B located between the holding portion 29 and the connector 15, and the water-supplying duct line 28A are disposed between the first surface 143a and the second surface 143b of the sheet 143 to be set in the concave portion 144b formed in the welding base 144a (FIG. 15(a)).

Thereafter, the welding base 144a is covered with a heater lid 144c. At the concave portion 144d formed in the heater lid 144c, the holding portion 29, connector 15, the universal cord 13B located between the holding portion 29 and the connector 15, and the water-supplying duct 28A are secured tightly between the first surface 143a and the second surface 143b of the sheet 143. The first surface 143a and the second surface 143b of the sheet 143 together with the operational portion cover 12A are then heated by the heater lid 144c for starting the welding operation (FIG. 15 (b)).

When the convex portion 144e formed at both ends of the concave portion 144d of the heater lid 144c is mounted on the welding base 144a, the heat from the convex portion 144e acts to melt away surplus portions of the first surface 143a and the second surface 143b of the sheet 143.

Figure 15C:
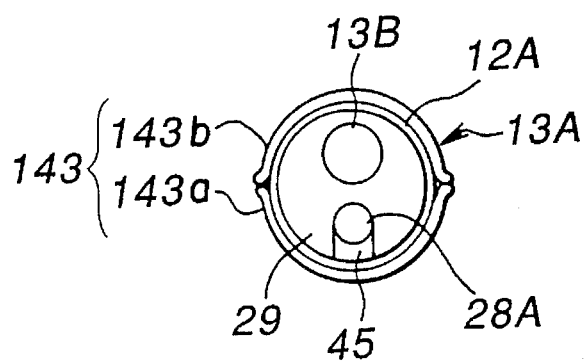

Subsequently, the periphery of the sheet 143 would be further welded, so as to complete the universal cord cover 13a (FIG. 15(c)).

The number 45 designates a spacer provided to hold the water-supplying duct line 28A after fitting the water-supplying duct line 28A to the holding portion 29.

Further, no disadvantage would arise even if burs are generated at the welded portion, since the universal cord cover 13A is not inserted into the body cavity so as not to undesirably affect it. Therefore, the surface of the universal cord cover need not be smooth. Although the sheet 143 would preferably be formed of the same material as that of the operational portion cover 12A, e.g. fluoro rubber, any other different material may be used.

As a related art, there has been known an apparatus in which the holding portion 29, the connector 15, the universal cord 13B and the water-supplying duct line 28A are covered with the universal cord cover 13A having been previously in a tucked up state on using the endoscope. However, since the universal cord is relatively long and has holding portion 29 and the connector 15 of relatively large contour mounted at both ends thereof, the cord cover fitting operation is difficult. In particular, when the fitting of the universal cord cover 13A is carried out during the interval of the case inspections, the troublesome cover fitting operation would cause a significant time loss, thereby reducing the number of inspectable cases for a day and to give a mental anguish to the patient. In view of such a problem, according to this embodiment, the universal cord cover 13A can be fitted in a short time and handled easily so as to increase the number of inspected cases for a day while reducing the pain and fatigue of the doctor and the patient.

Figure 16:
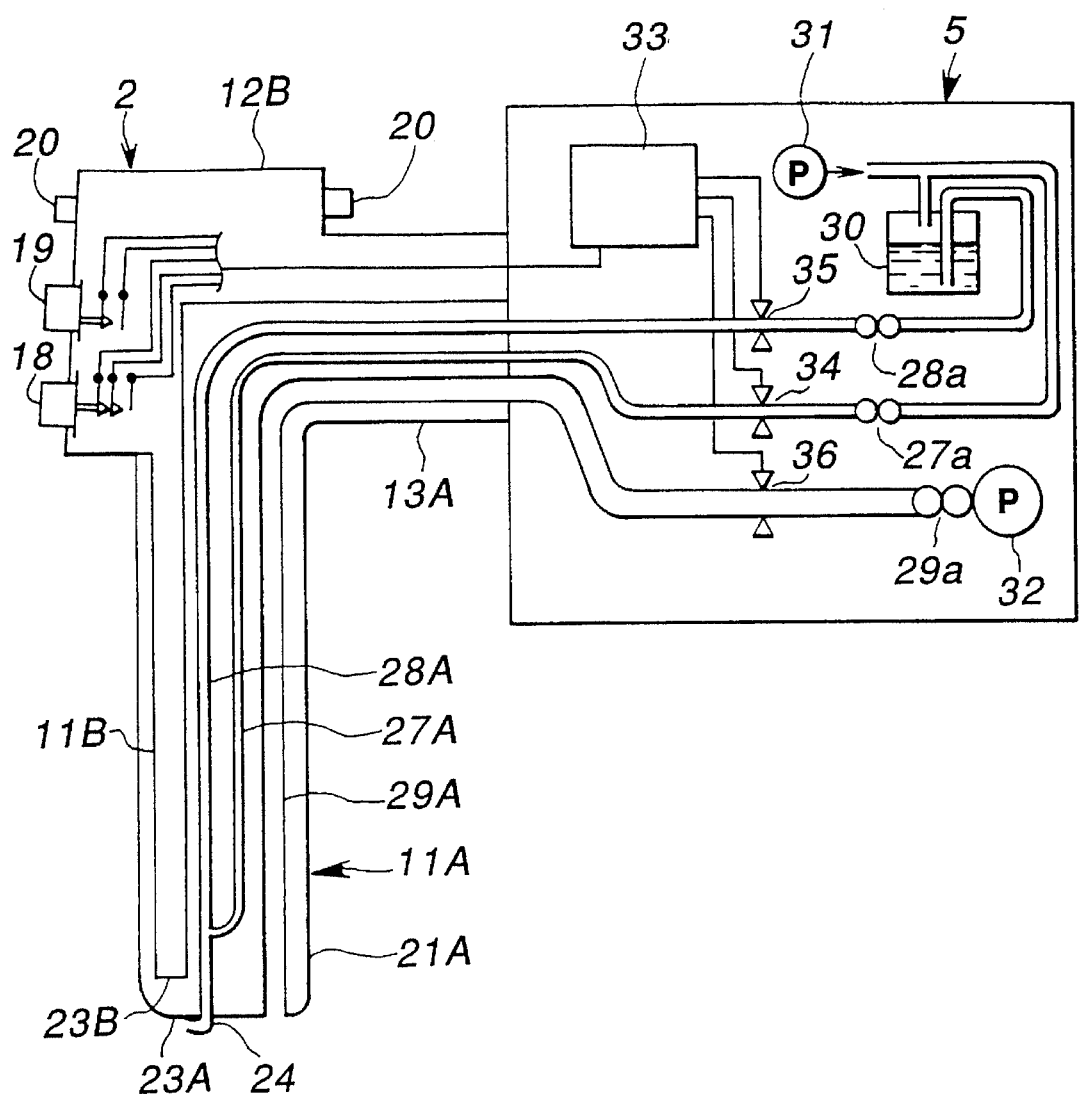
FIGS. 16 and 17 show a seventh embodiment of this invention.
Figure 17:
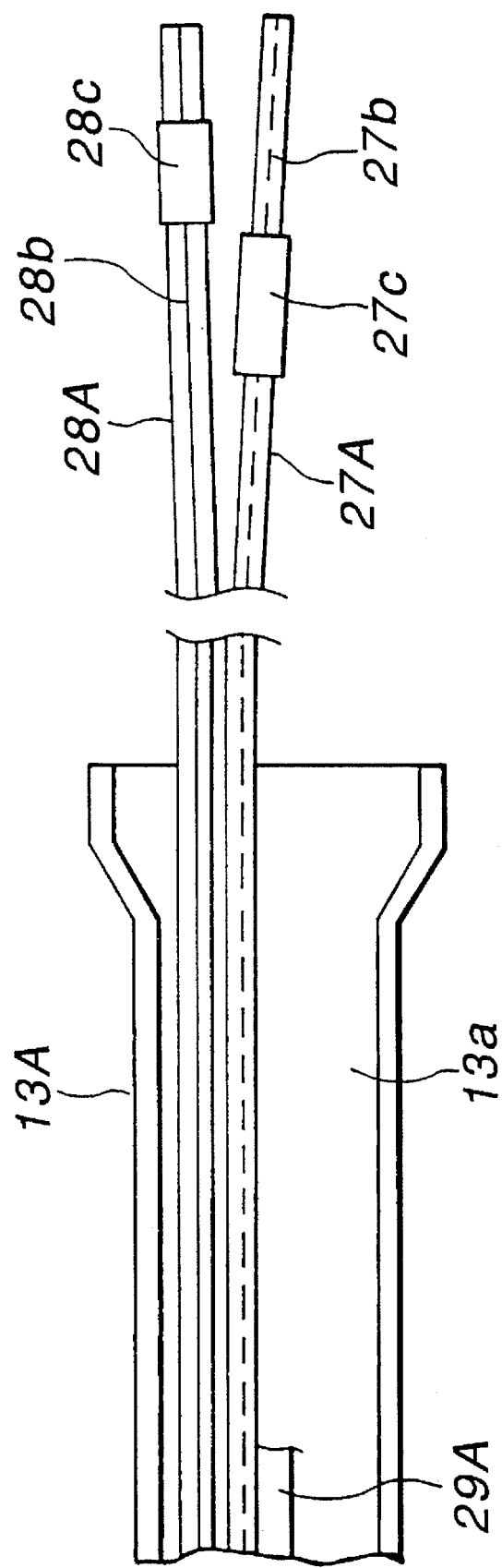

FIGS. 16 and 17 show a seventh embodiment of the present invention.

In this embodiment, as shown in FIG. 16, the air-supplying duct line 27A, the water-supplying duct line 28A and an aspiratory duct line 29A etc. are formed in the inserting portion-covering portion 11A. The air-supplying duct line 27A and the water-supplying duct line 28A are mated at the distal end side to communicate with the nozzle 24 provided at the end surface of the cover distal end portion 23A. The distal end opening of the nozzle 24 is opposed to the outer surface of the cover observing window 26A.

Further, the base end sides of the air-supplying duct line 27A, the water-supplying duct line 28A, and the aspirator duct line 29A are extended upwardly to the fluid controlling device 5 side from the mouth portion 22A for fixing the operational portion of the endoscope in a state of being covered with the universal cord cover 13A together with the universal cord 13B. The proximal end portions of the duct lines 27A, 28A and 29A projecting from the base end of the universal cord cover are connectable to an air supplying connecting portion 27a, a water-supplying connecting portion 28a and an aspiratory connecting portion 29a. The numeral 13a in FIG. 17 designates an inserting portion for inserting a universal cord 13B in the universal cord cover 13A.

The water-supplying connecting portion 28a faces the water-supplying tank 30. Meanwhile, the air-supplying connecting portion 27a is communicated with the air-supplying pump 31 and is branched at its intermediate section to face the upper part of the water-supplying tank. Further, the aspiratory connection section 29a is communicated with the aspiratory pump 32.

The air-supplying/water-supplying switch 18 is a double switch, in which a first depression opens the air-supplying electromagnetic valve 34 controlled by the controlling circuit 33 to start the air-supplying through the air-supplying pump 31, and a second depression opens the water-supplying electromagnetic valve 35 to supply water having been stored in the water-supplying tank 30. At this water-supplying, the air-supplying electromagnetic valve 34 may be either opened or closed.

Meanwhile, depression of the aspiration switch opens the aspiratory electromagnetic valve 36 to perform aspiration by the aspiratory pump 32.

Therefore, mucus having been attached to the cover observing window 26A could be removed therefrom by supplying air or water through the air-supplying duct line 27A or the water-supplying duct line 28A by the operation of the water-supplying/air-supplying switch 18.

The inner diameters of the air-supplying duct line 27A and the water-supplying duct line 28A are set in accordance with the flow amount of the fluid flowing through the duct lines 27A and 28A respectively. In the shown embodiment, the inner diameter of the air-supplying duct line 27A is less than the inner diameter of the water-supplying duct line 28A.

Further, as shown in FIG. 17, a discriminating means for discriminating the duct lines 27A and 28A is provided on at least the proximal side end portions of the air-supplying duct line 27A and the water-supplying duct line 28A. This discriminating means could be composed as any one or any combination of the following items (1)–(7):

(1) To change the colors of the duct lines 27A, 28A themselves;

(2) To form index lines 27b, 28b on the duct lines 27A, 28A and to change their colors;

(3) To change the kinds of lines of the index lines 27b, 28b;

(4) To attach identification labels 27c, 28c, on which colors, codes and marks for the identification are indicated, to the duct lines 27A, 28A respectively;

(5) To change the magnitude of the identification labels 27c, 28c;

(6) To change the position of attaching the identification labels 27c, 28c;

(7) To indicate the word "WATER" on the proximal end portion of the water-supplying duct line 28A or the identification label 28c, while the word "AIR" on the proximal end portion of the air-supplying duct line 27A or the identification label 27c.

The same identification means of (1)–(7) are also provided at the fluid controlling apparatus 5 side of the connecting portion 28a, 27a.

Meanwhile it is possible to provide the identification means on the aspiratory duct line 29A and the aspiratory connecting portion 29a but not necessary for identifying it from the other duct lines 27A, 28A.

The operation of this embodiment will now be described.

Upon determination of a covering endoscope 2B to be used, an endoscope cover 2A fitting to the covering endoscope 2B is selected.

When the covering endoscope 2B is inserted into the inserting portion-covering portion 11A of the selected cover 2A, the flange portion of the upper end of the mouth portion 22A for fixing the operational portion of the endoscope is held by the semicircular cover holding member 10a provided in the holder 10.

Then, an end of the dilatable tube 37 is coupled to the dilatable tube mouth 38 and the covering endoscope 2B is inserted into the opening 40, for dilating the inserting portion cover skin 21A for smooth attachment of the inserting portion 11B.

After completion of the inserting operation, when the end of the dilatable tube 37 is removed from the dilatable tube mouth 38, the cover skin 21A for the inserting portion would be contracted due to its elasticity (the outer diameter of the cover skin 21A for the inserting portion reduces), and the skin or the outer surface of the inserting portion 11B comes too closely attached to the inner surface of the skin 21A.

On the use of the cover-type endoscope 2 having been completed by a predetermined combination of the components, the end portions of the air-supplying duct line 27A, the water-supplying duct line 28A, the aspiratory duct line 29A which extend from the proximal end portion of the universal cord cover 13A of the endoscope cover 2A are connected to the air-supply connecting portion 27a, the water-supply connecting portion 28a, and the aspiratory connecting portion 29a at the fluid controlling device 5 side.

At this time, the correspondence of the duct lines to the connecting portions are confirmed by the indications of the identification means 27b, 28b, 27c, and 28c etc. provided at the proximal end portions of the air-supplying duct line 27A, water-supplying duct line 28A, and the connecting portions 27a, 28a. The connection for the aspiratory duct line 29A is also confirmed in the same manner. If the duct lines are of only three systems, the aspiratory duct line 29A could be easily identified without any identification means to be attached thereto.

As a result, the labor for confirming the correct connection can be reduced, and any mis-connection can be securely avoided.

Figure 18:
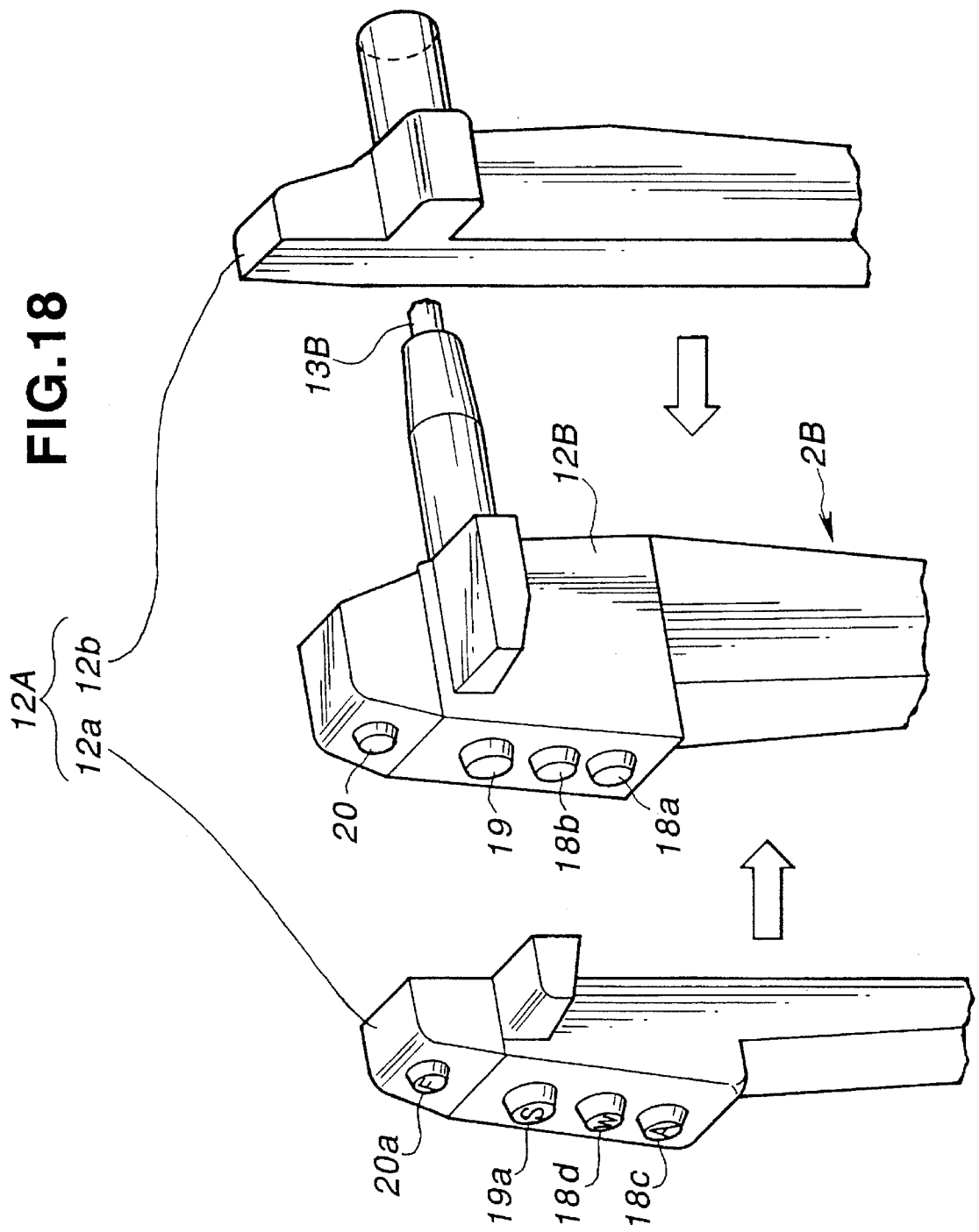
FIG. 18 is a perspective view showing an operational portion cover and an endoscope operational portion according to an eighth embodiment of this invention.

FIG. 18 shows an eighth embodiment of the present invention.

In this embodiment, the operational portion cover 12A of the endoscope cover 2A covering the operational portion 12B of the covering endoscope 2B is divided into two parts, an operational portion front cover 12a and an operation portion rear cover 12b. The front cover 12a is formed of an elastic material such as fluoro rubber or thin-film Teflon, while the rear cover 12b is formed of fluoro rubber, fluororesin, polysulfone, or silicon resin etc.

The inner surfaces of both the covers 12a, 12b are formed in a shape corresponding to the contour of the operational portion 12B. Therefore, the portions of the front cover 12a corresponding to the air-supplying switch 18a, the water-supplying switch 18b, the aspiratory switch 19 and the freeze switch being a image changing switch provided on the operational portion 12B are convexly formed. The switches 18a, 18b, 19 and 20 contain electrical switches therein respectively and having push button portions formed of fluororesin or silicon resin etc., and are watertightly mounted on the operational portion 12B. In FIG. 18, the water-supplying function and the air-supplying functions are of separate switch type as independent functions.

On the other hand, display portions 18c, 18d, 19a and 20a are provided at positions on the front cover 12a corresponding to the switches 18a, 18b, 19 and 20, for indicating the operational contents of these switches respectively. It is also possible to convexly and concavely form the display portions 18c, 18d, 19a and 20 integrally with the front cover 12a so as to enable the operator to identify the functions by finger touching. Alternatively, the display portions can be composed by adhering molded products of letters and marks as separate components. Further, if the front cover 12a is black color, the display portions 18c, 18d, 19a and 20a can be displayed in white color or by classification by colors in accordance with the functions. Namely, the indicating contents of the display portions 18c, 18d, 19a and 20a can be composed of codes, marks, colors etc., in addition to letters, which could distinguish the functions.

According to this embodiment, the functions of the switches 18a, 18b, 19 and 20 can be quickly recognized from the indication of the display portions 18c, 18d, 19a and 20a. Therefore, any mis-operation can be securely avoided, thereby proving a good handling property.

Figure 19:
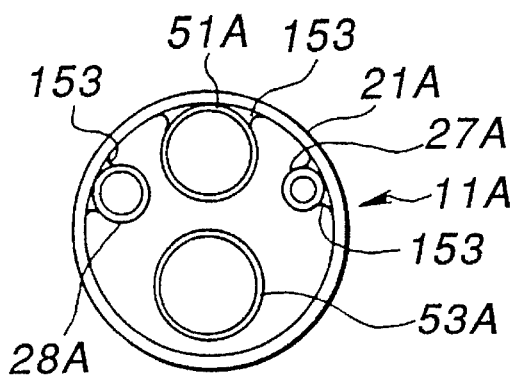

FIGS. 19 though 21 show a ninth embodiment of the present invention.

In this embodiment, as shown in FIG. 19, the duct lines such as the air-supplying duct line 27A, water-supplying duct line 28A, forceps channel 51A etc. are fixed by a fixing means 153 at one or more positions with a space therebetween. The fixing positions exclude the cover distal end portion 23A of the cover portion 11A for the inserting portion of the endoscope cover 2A, and are those not interfering with the inner surfaces of the cover skin 21A for the inserting portion of the cover portion 11A. As a result, even on the curving operation the duct lines do not meander, bend, twist or rupture such that the durability increases and unexpected damages etc. can be securely prevented.

An elastic adhesive agent would be preferable as the fixing means 153. Alternatively, it is also desirable to compose the duct lines 27A, 28A and 51A of the same material (e.g. fluororesin) as that of the cover portion 11A for the inserting portion, to be welded by heating. Further, as shown in FIG. 20, if it is desired to dispose the duct lines 27A, 28A, 51A and the cover skin 21A with a predetermined space therebetween, both can be adhered or welded with a predetermined space in the longitudinal direction by means of a spacer 152. The space by the spacer would preferably be ranged 3–50 cm.

The numerals shown designate respectively: 53A, an endoscope inserting channel; 51a, a forceps inserting opening; 51b, a forceps outlet; 54, a distal end composing portion of the endoscope provided at the distal end of the inserting portion of the cover-type endoscope 2B; 55, a signal line; 56, an articulation piece acting for the curving operation; 57, an articulation shaft; and 58, a solid-state imaging element.

Figure 21A:
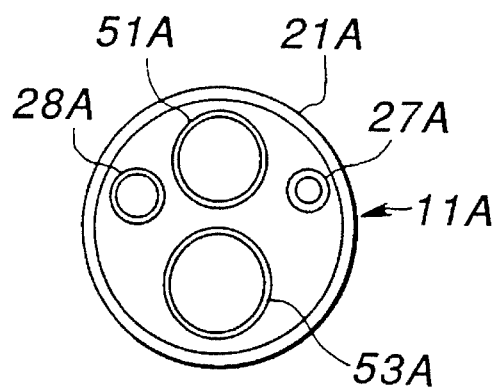
FIGS. 21(a) and 21(b) are cross-sectional views of an inserting portion-covering skin in relation to the ninth embodiment of this invention.

In addition, as a related art to this invention, there has been known an apparatus as shown in FIG. 21(a) in which the distal end sides of the duct lines 27A, 28A and 51A are fixed only at the cover distal end portion 23A. In such a structure, since the portions of the duct lines 27A, 28A and 51A other than the fixed portion can be freely moved within the cover skin 21A, when the distal end curving portion is curved the duct lines would mutually interfere to cause problems of bending, twisting or rupturing. Moreover, if, for example, the forceps channel 51A is bent, a corresponding treatment equipment such as a forceps cannot be smoothly inserted into the channel 51A, thereby impeding the inspection.

Figure 21B:
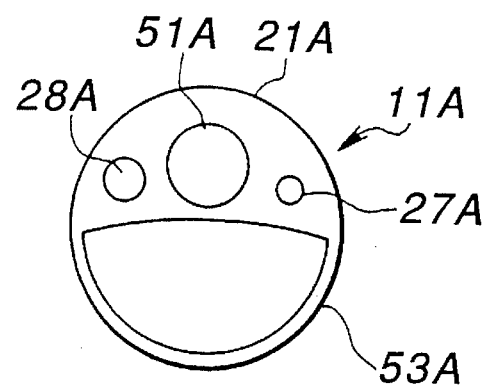

To cope with such a problem, there has been conventionally known a type of cover skin 21A composed of a multi-lumen tube integrating the duct lines 27A, 28A and 51A. However, in the multi-lumen tube, the flexibility of the distal curved portion of the inserting portion 11B of the covering endoscope 2B inserted into the channel 53A would vary depending on the vertical and horizontal directions etc. in FIG. 21(b). Since the flexibility of the cover skin 21A significantly affects the curving operational characteristics of the distal curved portion, the handling property thereof degrades. Furthermore, since the resistance of the curving portion becomes reduced when curved in a direction of less flexibility, the durability of the covering endoscope 2B would be reduced.

Also, as shown in FIG. 20, it is possible to enhance the assembling characteristics of the cover portion 11A for the inserting portion by setting the inner diameter of the cover skin 21A to be equal to or somewhat larger than the outer diameter of the cover skin mounting portion for the inserting portion provided on the mouth portion 22A for fixing the operational portion of the endoscope, when both ends of the cover skin 21A are watertightly fixed to the cover distal end portion 23A and the mouth portion 22A.

FIG. 22 shows a tenth embodiment of the present invention.

Aspiratory duct lines 29Aa, 29Ab of different diameters are selectively used in accordance with the type of the covering endoscope 2B to be combined. As shown in FIG. 22, a pinch valve tube 29a of the same size or the same standard with the aspiratory duct lines 29Aa, 29Ab is coupled to these aspiratory duct lines, and are then coupled to the aspiratory pump 32 through a pinch valve 136 which is an aspiratory electromagnetic valve of the fluid controlling apparatus being a common external connecting apparatus.

The pinch valve 136 interlocks with the aspiratory switch 19 etc. provided on the endoscope operational portion 12B, and is switched by rupturing the intermediate portion of the pinch valve tube 29a.

As a related art of the present invention, there has been known an apparatus in which the aspiratory duct lines 29Aa, 29Ab of different diameters are coupled to the aspiratory pump 32 through the pinch valve 136 of the fluid controlling apparatus 5. However, there is a limitation in the controllable diameter for the pinch valve 136 which cannot be applied to all types of the aspiratory duct lines 29Aa, 29Ab. Meanwhile, in the present embodiment, the pinch valve tube 29a of the same size or the same standard is used as the connecting portion so as to enable the fluid controlling apparatus to be used in common, thereby enhancing the handling characteristics.

Even if there are a number of duct lines extended from the universal cord cover 13A, at least the aspiratory duct line 29Aa or 29Ab would not be mis-connected to the fluid controlling device 5, since the pinch valve tube 29a to be used in common for the aspiratory duct lines 29Aa, 29Ab irrespective of the kind of the duct lines to be used.

In this embodiment, any duct line other than the aspiratory duct line 29A can be applied if it can make the connecting portion to be used in common.

In the present invention, it is obvious that a number of widely different embodiments can be composed according to the present invention without departing from the concept and the scope of this invention. The present invention is not limited to the particular embodiment, but only to the appended claims.

We claim:

1. A cover-type endoscope apparatus comprising:

an endoscope cover; and a covering endoscope used by inserting said covering endoscope into the endoscope cover, wherein there is provided a two-part display means for indicating a fit among a plurality of corresponding parameters of said endoscope cover and said covering endoscope, said two-part display means having a first part located on an operation portion of the covering endoscope and a second part at a side surface of an inserting-portion covering portion of said endoscope cover.

2. A cover-type endoscope apparatus according to claim 1, wherein said display means indicates a fit in the dimension of length of the covering endoscope in the observing direction.

3. A cover-type endoscope apparatus according to claim 1, wherein said display means indicates a fit in the dimension of an outer diameter of the covering endoscope.

4. A cover-type endoscope apparatus according to claim 1, wherein said display means indicates a fit in the dimension of a cross-sectional shape of the covering endoscope.

5. A cover-type endoscope apparatus according to claim 1, wherein said display means indicates a fit in at least one size dimension of a forceps channel.

6. A cover-type endoscope apparatus comprising:

an endoscope cover;

a covering endoscope used by inserting said covering endoscope into the endoscope cover; and an indication means having unevenness on a surface for indicating the operational contents of an operating means provided in an operational portion of the covering endoscope and having one or more different identifying colors, the endoscope cover being formed of a soft thin film resin which is transparent or translucent when viewed from outside the endoscope cover.

7. A cover-type endoscope apparatus comprising:

an operational portion of a covering endoscope;

an operational cover of an endoscope cover for covering the operational portion;

a curving operational knob shaft provided in the operational portion; and a curving operational knob mounted on the curved operational knob shaft, wherein said operational cover is large enough to cover the curved operational knob shaft on which the curving operational knob is not mounted, wherein the curving operational knob is mounted axially on said curving operational knob shaft wherein said curving operational knob shaft passes through a tight-fitting hole formed in said operational cover formed by a rupturing of said cover by said curving operational knob shaft at the point of said hole.

* * * * *